(12) United States Patent
Tarur et al.

(10) Patent No.: US 7,439,365 B2
(45) Date of Patent: Oct. 21, 2008

(54) PHARMACEUTICAL SALT OF (1-BENZYL-4-[(5,6-DIMETHOXY-1-INDANONE)-2-YL] METHYL PIPERIDINE (DONEPEZIL)

(75) Inventors: Venkatasubramanian Radhakrishnan Tarur, Mumbai (IN); Dhananjay Govind Sathe, Thane (IN); Avinash Venkatraman Naidu, Dombivli (IN); Umesh Parashram Aher, Kalyan (IN)

(73) Assignee: USV, Ltd., Mumbai (IN)

( * ) Notice: Subject to any disclaimer, the term of this patent is extended or adjusted under 35 U.S.C. 154(b) by 525 days.

(21) Appl. No.: 10/879,816

(22) Filed: Jun. 29, 2004

(65) Prior Publication Data

US 2005/0107613 A1 May 19, 2005

Related U.S. Application Data

(63) Continuation-in-part of application No. 10/714,724, filed on Nov. 17, 2003, now Pat. No. 6,953,856.

(51) Int. Cl.
*C07D 211/02* (2006.01)

(52) U.S. Cl. ........................ 546/206; 514/319; 546/205

(58) Field of Classification Search ................. 514/319; 546/205, 206
See application file for complete search history.

(56) References Cited

U.S. PATENT DOCUMENTS 6,245,911 B1    6/2001 Imai

OTHER PUBLICATIONS

Rouhi et al. "The right stuff" Chem. eng. New, Feb. 2003, p. 32-35.*
Berge et al. "Pharmaceutical salts" J. Phar. Sci. v.66, p. 1-19 (1977).*
Conyers et al. "The relation of clinical catastrophes . . . " CA 113:228637 (1990).*
Lenin et al. "Attenuation of oxalate . . . " CA 137:103659 (2002).*
Jain et al. "Polynmorphism in parmacy" INdan Drugs, 23(6) p. 315-329 (1986).*
Otsuka et al. "Effect of polymorphic forms of . . . " Chem. Pharm. Bull 47(6) 852-856 (1999).*
Taday et al. "Using terahertz pulse spectroscopy . . . " J. Pharm Sci. 92(4) 831-838 (2003).*
Exhibit A and B.*

* cited by examiner

*Primary Examiner*—Celia Chang
(74) *Attorney, Agent, or Firm*—Pharmaceutical Patent Attorneys, LLC (57) ABSTRACT

The present invention relates to the oxalate salt of 1-benzyl-4-[(5,6-dimethoxy-1-indanone)-2-yl]methyl piperidine, commonly known as Donepezil, and its method of preparation.

20 Claims, 6 Drawing Sheets

PHARMACEUTICAL SALT OF (1-BENZYL-4-[(5,6-DIMETHOXY-1-INDANONE)-2-YL] METHYL PIPERIDINE (DONEPEZIL)

RELATED APPLICATIONS

This application is a continuation-in-part of U.S. application Ser. No. 10/1714,724, filed Nov. 17, 2003, now U.S. Pat. No. 6,953,856.

The following specification describes the nature of this invention and the manner in which it is to be performed.

GOVERNMENT INTEREST

None.

TECHNICAL FIELD

The present invention relates to the oxalate salt of 1-benzyl-4-[(5,6-dimethoxy-1-indanone)-2-yl]methyl piperidine commonly known as Donepezil (I) and its method of preparation.

BACKGROUND & PRIOR ART

The process for the preparation of 1-benzyl-4-[(5,6-dimethoxy-1-indanone)-2-yl]methyl piperidine has been described in JP A-64-79151 (U.S. Pat. No. 4,895,841, EP 296560).

Japanese patent application, publication No. A64-79151 (U.S. Pat. No. 4,895,841, EP 296560) discloses certain salts of Donepezil, 1-benzyl-4-[(5,6-dimethoxy-1-indanone)-2-yl]methyl piperidine and in particular the hydrochloride salt having an excellent action as a prophylactic and a therapeutic agent for senile dementia, and in particular as a prophylactic and therapeutic agent for Alzheimer's disease and an industrial process for producing the same.

The compound Donepezil, {(1-benzyl-4-[(5,6-dimethoxy-1-indanone)-2-yl]methyl piperidine}, hereinafter is referred as compound R.

(R)

BRIEF DESCRIPTION

It has been discovered that compound (R) can be formed into a novel oxalate salt. The novel salt can be prepared by an efficient, economic and reproducible process and particularly suited to large-scale preparation. The oxalate salt is therefore surprisingly amenable to large scale pharmaceutical processing and formulation.

The present invention also relates to three novel polymorphic forms (I, II and III) of Donepezil oxalate, which are characterized by powder X-ray diffraction and or infrared absorption peaks recorded in potassium bromide.

Polymorphic crystals of compound (R) oxalate are hereafter referred as Oxalate form (I), Oxalate form (II) and Oxalate form (III).

The oxalate provides a melting point in the range of from 170 to 180° C., such as 175 to 180° C., for Oxalate form (I) and Oxalate form (II), and a melting point in the range of from 95 to 96° C. for Oxalate form (III).

The present invention encompasses the oxalate salts isolated in a purified form. Also, the invention provides the oxalate salts in a pharmaceutically-acceptable form, especially in bulk form, such form having good flow properties, especially good bulk flow properties.

The invention also provides a process for the preparation of the oxalate, in which 1-benzyl-4-[(5,6-dimethoxy-1-indanone)-2-yl]methyl piperidine (compound R) is preferably dispersed or dissolved in a suitable solvent and reacted with oxalic acid; and thereafter the oxalate formed is recovered by filtration.

A suitable solvent is an alkanol, for example propan-2-ol, or a hydrocarbon, such as toluene, a ketone, such as acetone, an ester, such as ethyl acetate, an ether such as tetrahydrofuran, a nitrile such as acetonitrile, a halogenated hydrocarbon such as dichloromethane.

The concentration of compound (R) is preferably in the range of from 3 to 25% weight/volume, more preferably in the range of from 5 to 20%. The concentration of oxalic acid solution is preferably in the range of from 3 to 50% weight/volume.

The reaction is usually carried out at ambient temperature or at an elevated temperature, although any convenient temperature that provides the required product may be employed. A preferred temperature is in the range of about 20 to about 120° C., such as 40° C. to 90° C., or more preferably about 70° C.

Oxalate Form (I) Crystals

Figure 1:
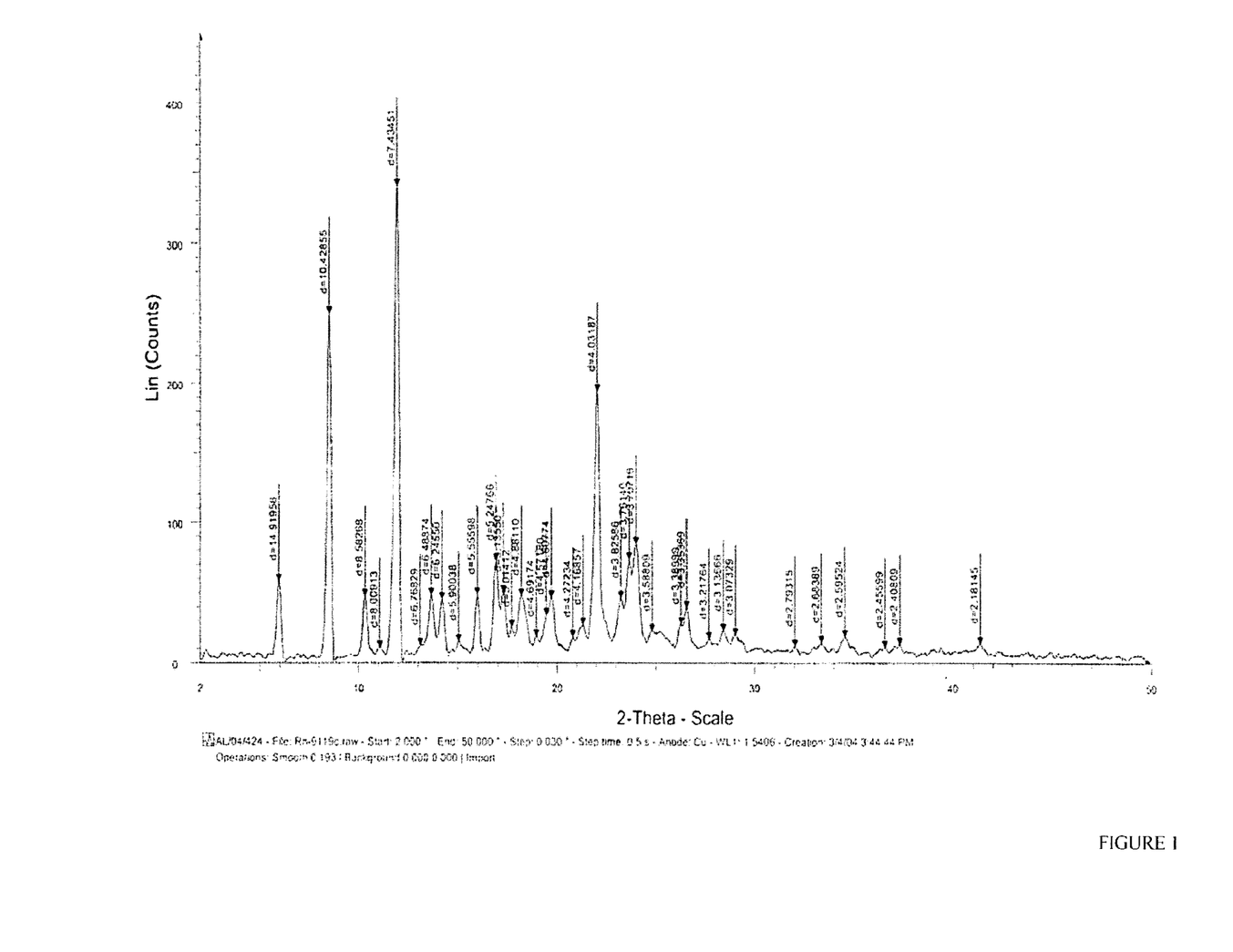
FIG. 1 shows a powder X-ray diffraction pattern for Oxalate form (I) crystals.
Figure 4:
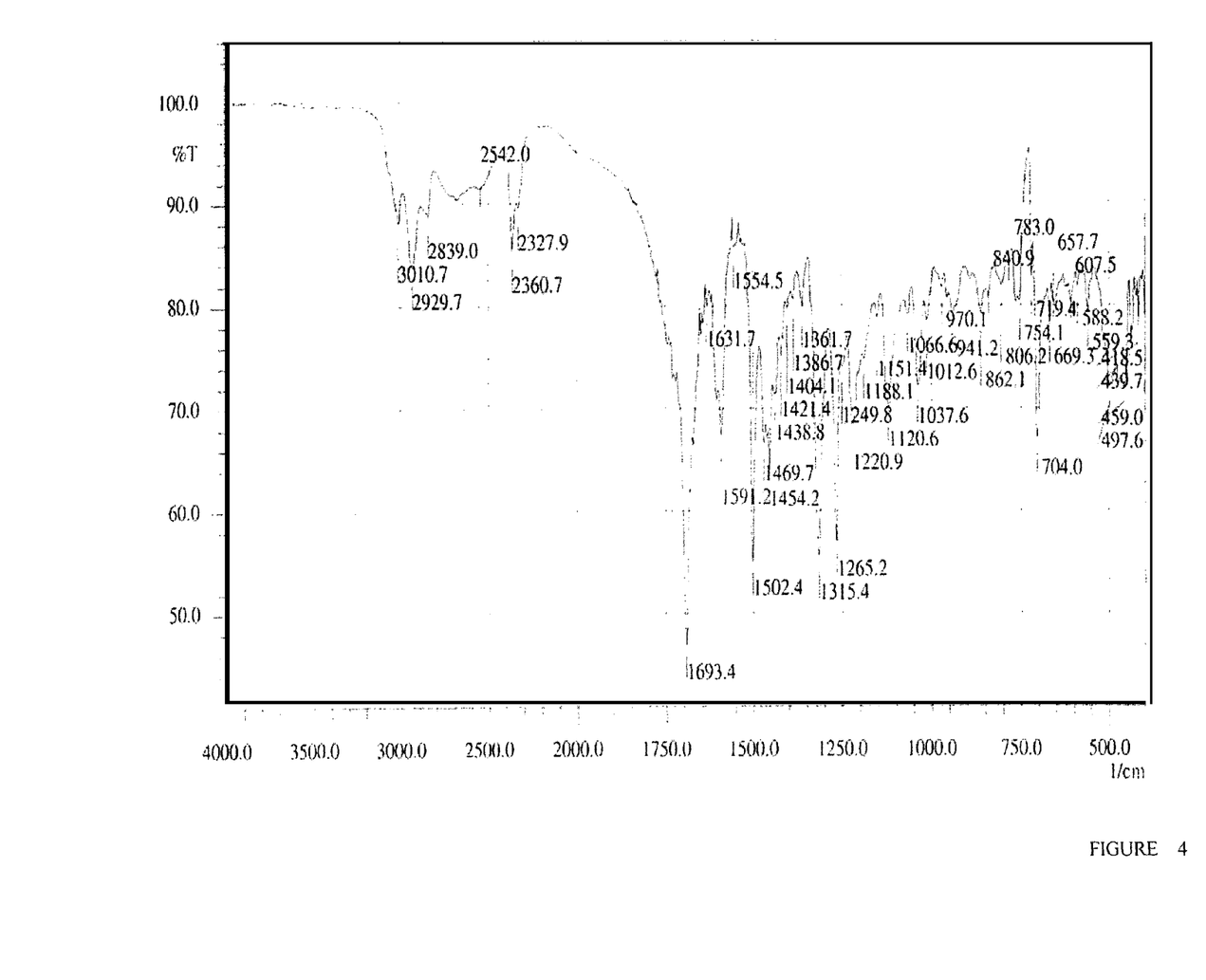
FIG. 4 shows an infrared absorption spectrum for Oxalate form (I) crystals.

The powder X-ray diffraction pattern of oxalate form I crystals is shown in FIG. 1. The infrared absorption spectrum for the same polymorphic form as recorded in potassium bromide, is shown in FIG. 4.

Oxalate Form (II) Crystals

Figure 2:
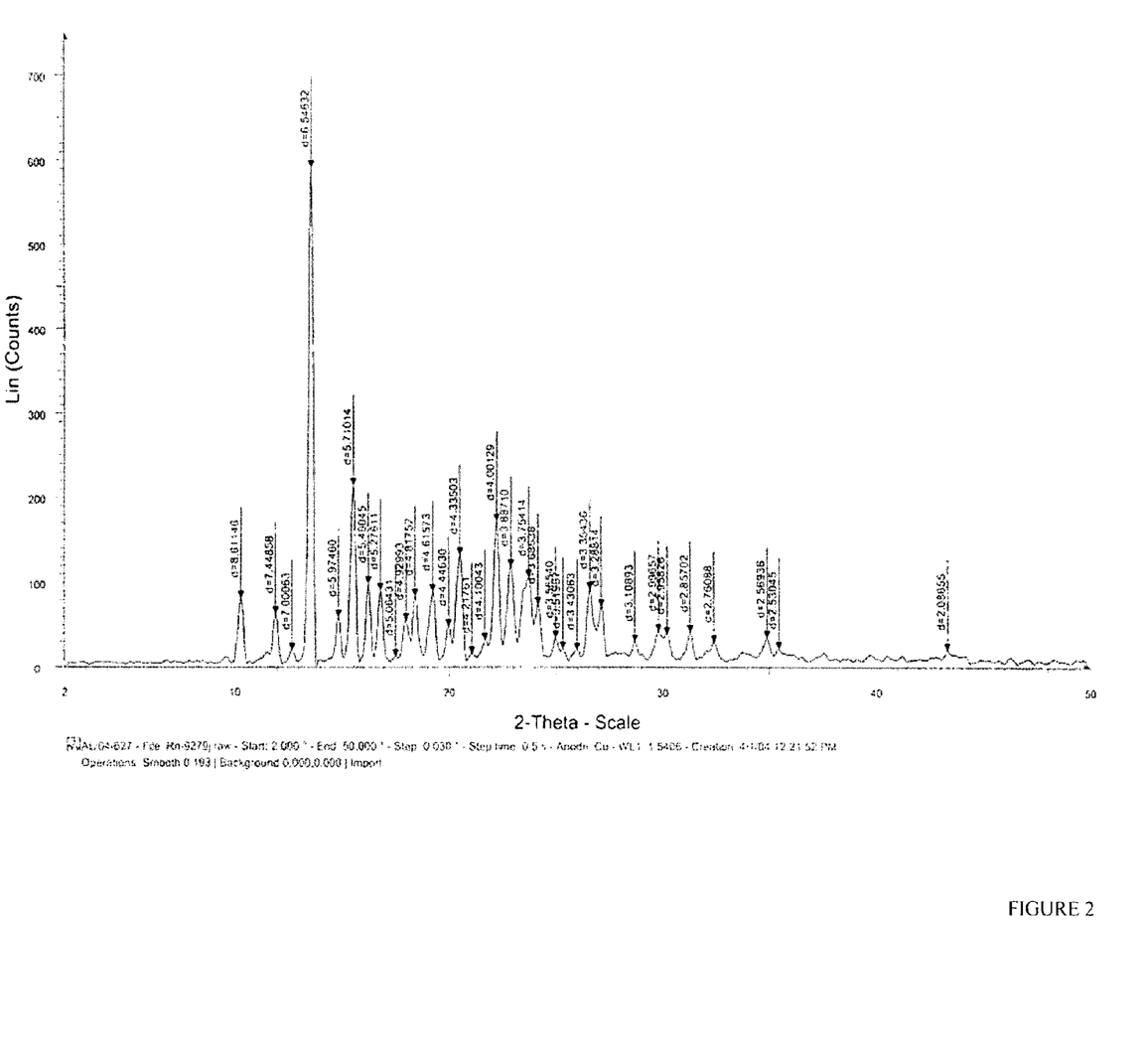
FIG. 2 shows a powder X-ray diffraction pattern for Oxalate form (II) crystals.
Figure 5:
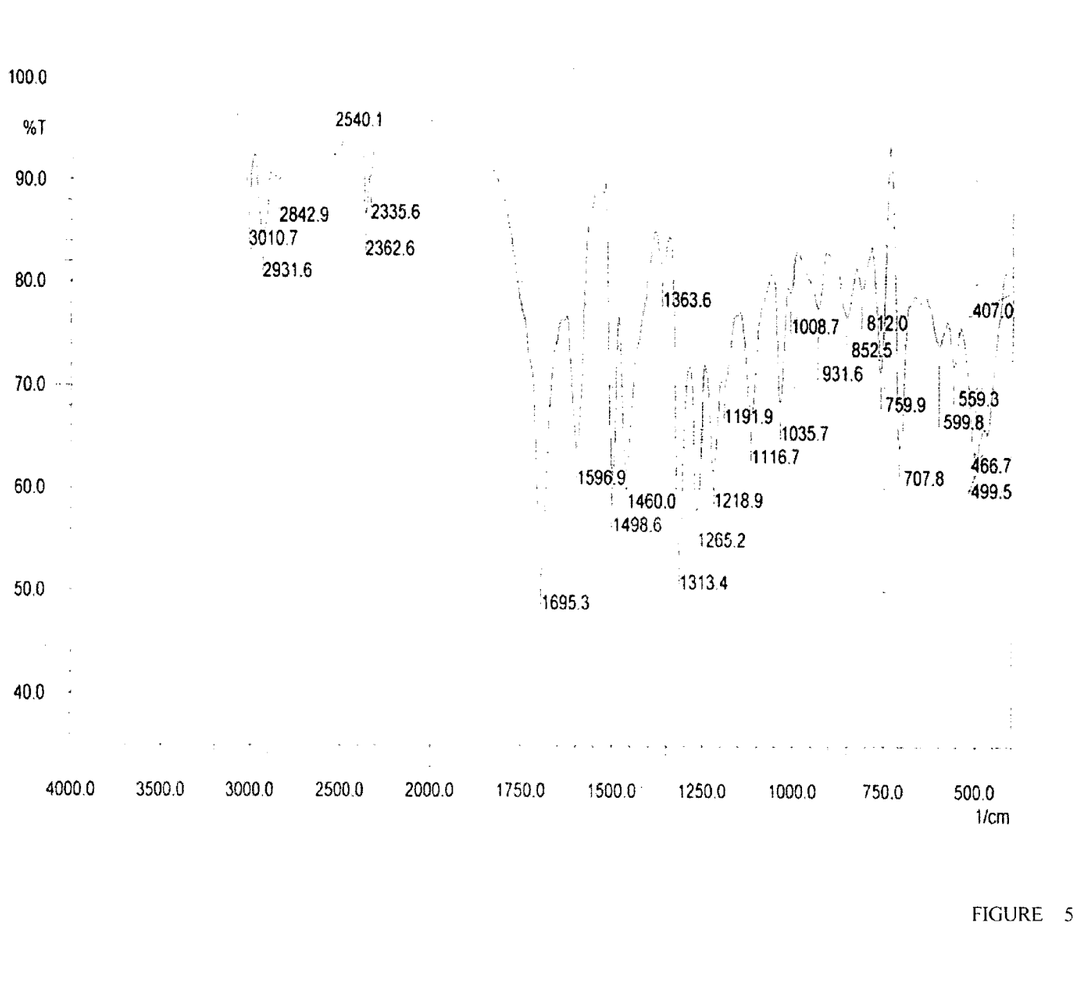
FIG. 5 shows an infrared absorption spectrum for Oxalate form (II) crystals.

The powder X-ray diffraction pattern of oxalate form II crystals is shown in FIG. 2. The infrared absorption spectrum for the same polymorphic form, as recorded in potassium bromide, is shown in FIG. 5.

Oxalate Form (III) Crystals

Figure 3:
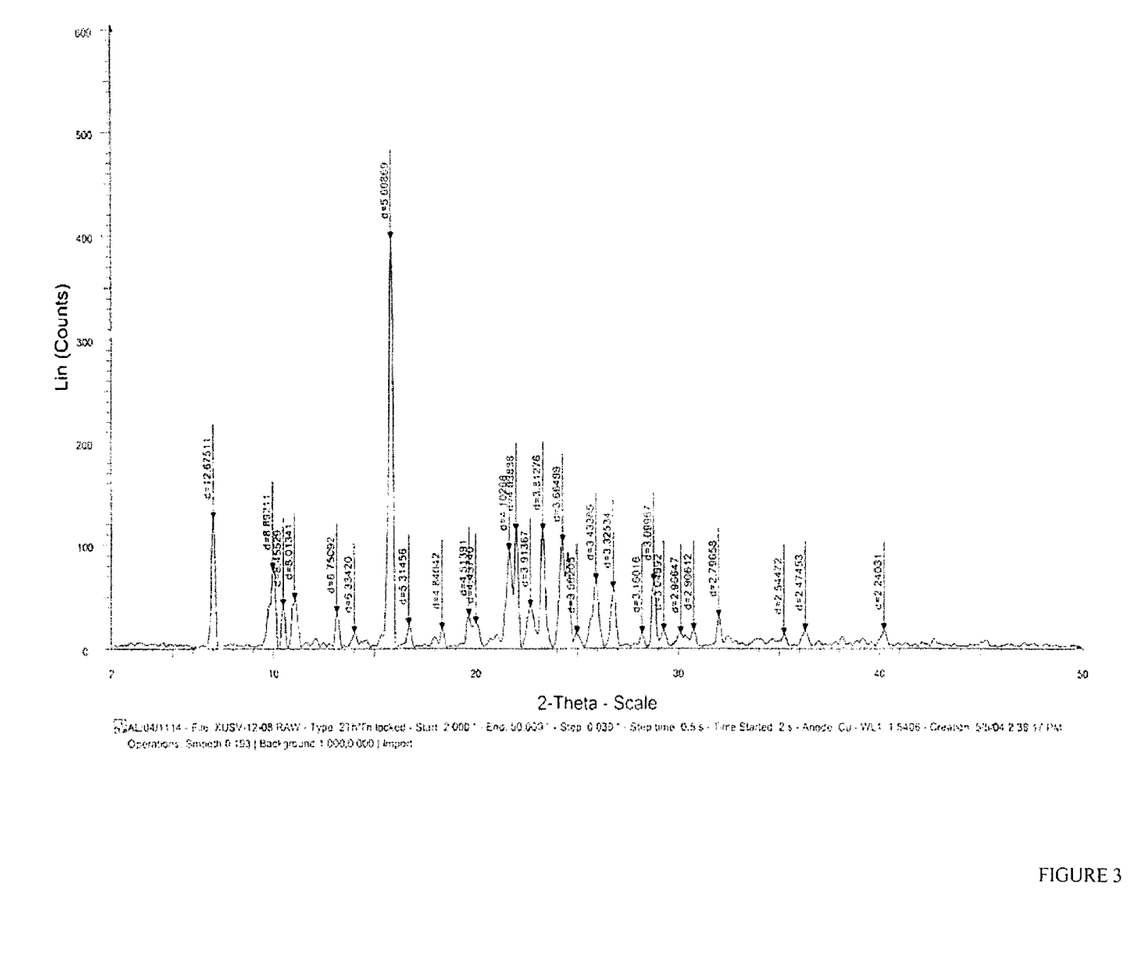
FIG. 3 shows a powder X-ray diffraction pattern for Oxalate form (III) crystals.
Figure 6:
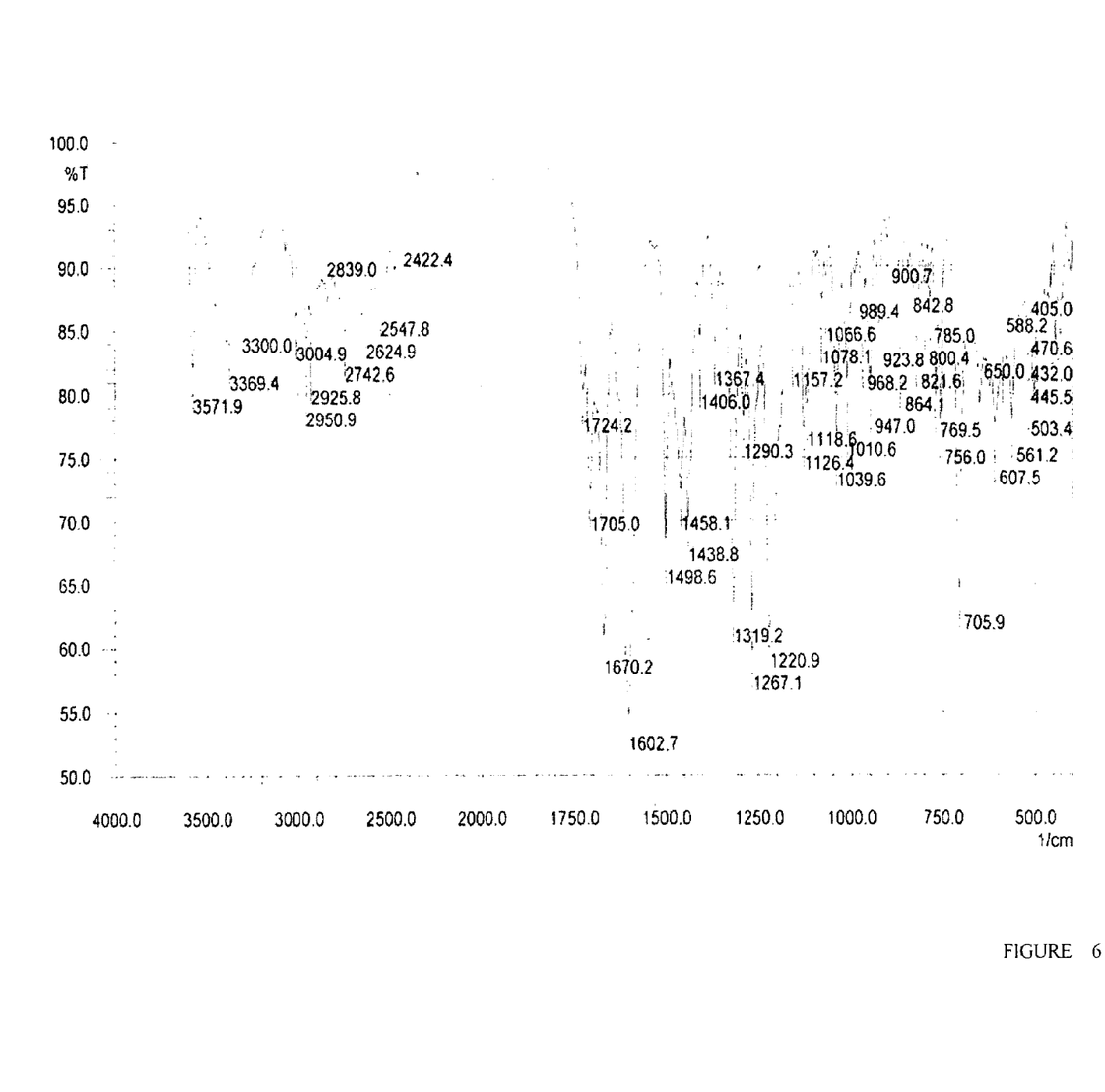
FIG. 6 shows an infrared absorption spectrum for Oxalate form (II) crystals.

The powder X-ray diffraction pattern of oxalate form III crystals is shown in FIG. 3. The infrared absorption spectrum for the same polymorphic form, as recorded in potassium bromide, is shown in FIG. 6.

Detail processes for preparing the novel oxalate salts are given below, wherein donepezil base is prepared by a process as described in U.S. Pat. No. 6,649,765 B1; this document is incorporated here by reference.

We discuss below eighteen Examples. The Examples first teach various methods to prepare donezepil oxalate. The Examples then teach various ways to process donezepil oxalate to make each of the three polymorphic forms of it. Here is a "Table of Contents" for the Examples which follow below:

Preparing Donezepil Oxalate:

Example 1: Process for preparing Donepezil oxalate by addition of oxalic acid in acetone to Donepezil base in ethyl acetate.

Example 2: Process for preparing Donepezil oxalate by addition of oxalic acid in Propan-2-ol to Donepezil base in ethyl acetate.

Example 3: Process for preparing Donepezil oxalate by addition of oxalic acid in methanol to Donepezil base in ethyl acetate.

Modifying Donezepil Oxalate to Make Polymorph Oxalate Form (I) Crystals

Example 4: Dissolving Donepezil oxalate in Methanol, followed by addition of Diethyl ether.

Example 5: Dissolving Donepezil oxalate in Methanol, followed by addition of Diisopropyl ether.

Example 6: Dissolving Donepezil oxalate in Ethanol, followed by addition of Diisopropyl ether.

Example 7: Dissolving Donepezil oxalate in Acetone, followed by addition of water.

Example 8: Dissolving Donepezil oxalate in Water, followed by addition of propan-2-ol.

Example 9: Dissolving Donepezil oxalate in Ethanol, followed by addition of n-hexane.

Example 10: Dissolving Donepezil oxalate in Methanol and cooling below 10° C.

Example 11: Dissolving Donepezil oxalate in Methanol, followed by addition of Toluene.

Example 12: Dissolving Donepezil oxalate in water, followed by addition of Acetonitrile.

Example 13: Dissolving Donepezil oxalate in Tetrahydrofuran, followed by addition of diisopropyl ether.

The above-mentioned Examples teach that the donepezil oxalate salt is dissolved in the respective solvents by heating at 40 to 60° C.

Modifying Donepezil Oxalate to Make Polymorph Oxalate Form (II) Crystals:

Example 14: Dissolving Donepezil oxalate in Dichloromethane, followed by addition of toluene.

Example 15: Dissolving Donepezil oxalate in Dimethyl formamide and cooling below 10° C.

Example 16: Dissolving Donepezil oxalate in Dichloromethane, followed by addition of Ethyl acetate.

The above mentioned Examples teach that the donepezil oxalate salt is dissolved in the respective solvents by heating at 40 to 60° C.

Modifying Donezepil Oxalate to Make Polymorph Oxalate Form (III) Crystals:

Example 17: Dissolving Donepezil oxalate in water and kept at room temperature (RT) for 72 hrs.

Example 18: Dissolving Donepezil oxalate in Methanol-water mixture kept at RT for 72 hrs.

The above-mentioned Examples teach that the donepezil oxalate salt is dissolved in respective solvents by heating at 40 to 60° C. The oxalate form (I) polymorphic form is identifiable by a characteristic powder x-ray diffraction. These peaks in the powder x-ray diffraction pattern are roughly as follows:

| Sr. No | Diffraction Angle (2 θ°) | Intensity % (I/Io) |
|---|---|---|
| 1. | 5.92 | 17.0 |
| 2. | 8.47 | 73.4 |
| 3. | 10.30 | 13.8 |
| 4. | 11.04 | 3.0 |
| 5. | 11.89 | 100.0 |
| 6. | 13.07 | 3.5 |
| 7. | 13.74 | 14.0 |
| 8. | 14.17 | 13.2 |
| 9. | 15.00 | 4.4 |
| 10 | 15.94 | 14.1 |
| 11 | 16.88 | 21.2 |
| 12 | 17.25 | 14.6 |
| 13 | 17.67 | 7.3 |
| 14 | 18.16 | 13.9 |
| 15 | 18.90 | 5.3 |
| 16 | 19.40 | 9.9 |
| 17 | 19.67 | 13.5 |
| 18 | 20.77 | 5.2 |
| 19 | 21.29 | 7.8 |
| 20 | 22.02 | 57.0 |
| 21 | 23.23 | 13.4 |
| 22 | 23.63 | 21.5 |
| 23 | 23.98 | 24.7 |
| 24 | 24.79 | 6.5 |
| 25 | 26.26 | 7.9 |
| 26 | 26.55 | 11.3 |
| 27 | 27.70 | 4.8 |
| 28 | 28.43 | 6.5 |
| 29 | 29.03 | 5.6 |
| 30 | 32.01 | 3.3 |
| 31 | 33.35 | 4.1 |
| 32 | 34.53 | 5.3 |
| 33 | 36.55 | 3.0 |
| 34 | 37.31 | 3.7 |
| 35 | 41.35 | 3.9 |

For the same polymorph, the wave numbers ($cm^{-1}$) of infrared absorption spectra recorded in potassium bromide are approximately as follows: 3010.7, 2931.6, 2842.9, 2540.1, 2362.6, 2335.6, 1695.3, 1596.9, 1498.6, 1460.0, 1363.6, 1313.4, 1265.2, 1218.9, 1191.9, 1116.7, 1035.7, 1008.7, 931.6, 852.5, 812.0, 759.9, 707.8, 599.8, 559.3, 499.5, 466.7 and 407.0.

The oxalate form (II) polymorphic form is identifiable by a characteristic powder x-ray diffraction. These peaks in the powder x-ray diffraction pattern are approximately as follows:

| Sr. No | Diffraction Angle (2 θ°) | Intensity % (I/Io) |
|---|---|---|
| 1. | 10.264 | 13.6 |
| 2. | 11.872 | 10.5 |
| 3. | 12.634 | 3.2 |
| 4. | 13.515 | 100 |
| 5. | 14.815 | 9.8 |
| 6. | 15.506 | 36.1 |
| 7. | 16.219 | 16.5 |
| 8. | 16.790 | 15.2 |
| 9. | 17.498 | 1.9 |
| 10. | 17.979 | 9.2 |
| 11. | 18.402 | 14.0 |
| 12. | 19.214 | 15.0 |
| 13. | 19.953 | 8.0 |
| 14. | 20.471 | 22.2 |
| 15. | 21.047 | 2.5 |
| 16. | 21.656 | 5.2 |

-continued

| Sr. No | Diffraction Angle (2 θ°) | Intensity % (I/Io) |
|---|---|---|
| 17. | 22.199 | 29.0 |
| 18. | 22.860 | 19.9 |
| 19. | 23.681 | 17.9 |
| 20. | 24.123 | 12.5 |
| 21. | 24.954 | 5.6 |
| 22. | 25.282 | 3.5 |
| 23. | 25.951 | 3.3 |
| 24. | 26.552 | 15.4 |
| 25. | 27.097 | 12.0 |
| 26. | 28.691 | 4.9 |
| 27. | 29.791 | 7.0 |
| 28. | 30.186 | 6.4 |
| 29. | 31.283 | 6.9 |
| 30. | 32.402 | 4.8 |
| 31. | 34.892 | 5.7 |
| 32. | 35.446 | 3.5 |
| 33. | 43.329 | 3.2 |

For the same polymorph, the wave numbers (cm$^{-1}$) of infrared absorption spectra recorded in potassium bromide are approximately as follows: 418.5, 439.7, 459.0, 497.6, 559.3, 588.2, 669.3, 704.0, 719.4, 754.1, 806.2, 862.1, 941.2, 1012.6, 1037.6, 1066.6, 1120.6, 1151.4, 1188.1, 1220.9, 1249.8, 1265.2, 1315.4, 1361.7, 1386.7, 1404.1, 1421.4, 1438.8, 1454.2, 1469.7, 1502.4, 1554.5, 1591.2, 1631.7, 1693.4, 2327.9, 2360.7, 2542.0, 2839.0, 2929.7, and 3010.7.

The Oxalate form (III) polymorphic form is identifiable by a characteristic powder x-ray diffraction. These peaks in the powder x-ray diffraction pattern are approximately as follows:

| Sr. No | Diffraction Angle (2 θ°) | Intensity % (I/Io) |
|---|---|---|
| 1. | 6.968 | 31.5 |
| 2. | 9.939 | 19.0 |
| 3. | 10.454 | 10.2 |
| 4. | 11.032 | 11.8 |
| 5. | 13.104 | 8.4 |
| 6. | 13.970 | 3.6 |
| 7. | 15.788 | 100 |
| 8. | 16.668 | 5.6 |
| 9. | 18.314 | 4.5 |
| 10. | 19.651 | 7.8 |
| 11. | 19.994 | 6.0 |
| 12. | 21.644 | 23.6 |
| 13. | 21.992 | 28.5 |
| 14. | 22.702 | 10.0 |
| 15. | 23.312 | 28.6 |
| 16. | 24.266 | 25.8 |
| 17. | 24.978 | 3.5 |
| 18. | 25.926 | 16.3 |
| 19. | 26.788 | 14.5 |
| 20. | 28.216 | 3.8 |
| 21. | 28.779 | 16.2 |
| 22. | 29.268 | 4.2 |
| 23. | 30.101 | 3.5 |
| 24. | 30.741 | 4.3 |
| 25. | 31.977 | 7.5 |
| 26. | 35.240 | 3.2 |
| 27. | 36.274 | 4.8 |
| 28. | 40.222 | 4.4 |

For the same polymorph, the wave numbers (cm$^{-1}$) of infrared absorption spectra recorded in potassium bromide are approximately as follows: 405, 432, 445.5, 470.6, 503.4, 561.2, 588.2, 607.5, 650, 705.9, 756, 769.5, 785.0, 800.4, 821.6, 864.1, 900.7, 923.8, 947.0, 968.2, 989.4, 1010.6, 1039.6, 1066.6, 1078.1, 1118.6, 1126.4, 1157.2, 1220.9, 1267.1, 1290.3, 1319.2, 1367.4, 1406.0, 1438.8, 1458.1, 1498.6, 1602.7, 1670.2, 1705.0, 1724.2, 2422.4, 2547.8, 2624.9, 2742.6, 2839.0, 2925.8, 2950.9, 3004.9, 3300, 3369.4, and 3571.9.

EXAMPLES

Examples 1 to 3: Production of Donepezil Oxalate.
Examples 4 to 13: Production of Polymorphic Crystals of Oxalate Form (I).
Examples 14 to 16: Production of Polymorphic Crystals of Oxalate Form (II).
Examples 17 to 18 Production of Polymorphic Crystals of Oxalate Form (III).

The present invention will now be described in more detail with reference to the following examples. It is needless to say that the technical scope of the present invention is not limited to these examples.

Example 1

To Donepezil base (obtained after benzylation; benzylation is known in the art, and is taught by, e.g., U.S. Pat. No. 6,649,765) (10 gms.) in ethyl acetate (200 ml) was added oxalic acid (5 gms dissolved in 100 ml acetone) slowly with stirring. After addition the reaction mass was concentrated in vacuum. The solid separated was filtered and washed with acetone and dried at 60° C. afforded the title compound with a yield of 12 gms (90.2%) and melting point 176-77° C.

Example 2

To Donepezil base (obtained after benzylation) (10 gms.) in ethyl acetate (200 ml) was added oxalic acid (5 gms dissolved in 100 ml propan-2-ol) slowly with stirring. After addition the reaction mass was concentrated in vacuum. The solid separated was filtered and washed with acetone and dried at 60° C. afforded the title compound with a yield of 12.5 gms (96.9%) and melting point 176-78° C.

Example 3

To Donepezil base (obtained after benzylation) (10 gms.) in ethyl acetate (200 ml) was added oxalic acid (5 gms dissolved in 100 ml Methanol) slowly with stirring. After addition the reaction mass was concentrated in vacuum. To the residue was added 50 ml propan-2-ol. The solid separated was filtered and washed with propan-2-ol and dried at 70° C. afforded the title compound with a yield of 12 gms, 90.2%.

Example 4

Donepezil oxalate (any form) 5 gms was dissolved in Methanol 50 ml under heating at 50° C. Under stirring, at room temperature 50 ml diethyl ether was added. Stirring was continued for 1 hour after the separation of the crystals. Filtration of the crystals and drying at 60° C. afforded the title compound with a yield of 4.5 gms (90%) and melting point 177-78° C.

Example 5

Donepezil oxalate (any form) 5 gms was dissolved in Methanol 50 ml under heating at 50° C. Under stirring, at room temperature 50 ml diisopropyl ether was added. Stirring was continued for 1 hour after the separation of the crystals.

Filtration of the crystals and drying at 60° C. afforded the title compound with a yield of 4.0 gms (80%) and melting point 177-78° C.

Example 6

Donepezil oxalate (any form) 5 gms was dissolved in Ethanol 50 ml under heating at 50° C. Under stirring, at room temperature 50 ml diethyl ether was added. Stirring was continued for 1 hour after the separation of the crystals. Filtration of the crystals and drying at 60° C. afforded the title compound with a yield of 4.2 gms (84%) and melting point 176-78° C.

Example 7

Donepezil oxalate (any form) 5 gms was dissolved in water 50 ml at room temperature. Under stirring, at 50° C. 100 ml acetone was added. Stirring was continued for 1 hour after the separation of the crystals. Filtration of the crystals and drying at 60° C. afforded the title compound with a yield of 4.1 gms (82%) and melting point 177-78° C.

Example 8

Donepezil oxalate (any form) 5 gms was dissolved in water 50 ml at room temperature. Under stirring, at 50° C. 100 ml propan-2-ol was added. Stirring was continued for 2 hour after the separation of the crystals at 15° C. Filtration of the crystals and drying at 60° C. afforded the title compound with a yield of 4.6 gms (92%) and melting point 176-78° C.

Example 9

Donepezil oxalate (any form) 5 gms was dissolved in ethanol 50 ml under heating at 50° C. Under stirring, at 50° C. 50 ml n-hexane was added. Stirring was continued for 1 hour after the separation of the crystals. Filtration of the crystals and drying at 60° C. afforded the title compound with a yield of 4.4 gms (88%) and melting point 177-78° C.

Example 10

Donepezil oxalate (any form) 5 gms was dissolved in methanol 25 ml under heating at 50° C. Stirring was continued for 1 hour with gradual cooling. Stirring was further continued for 1 hour after the separation of the crystals at room temperature. Filtration of the crystals and drying at 60° C. afforded the title compound with a yield of 4.0 gms (80%) and melting point 177-78° C.

Example 11

Donepezil oxalate (any form) 5 gms was dissolved in methanol 50 ml under heating at 50° C. Under stirring, at 50° C. 100 ml toluene was added. Stirring was continued for 1 hour with gradual cooling. Stirring was further continued for 1 hour after the separation of the crystals. Filtration of the crystals and drying at 60° C. afforded the title compound with a yield of 4.4 gms (88%) and melting point 177-78° C.

Example 12

Donepezil oxalate (any form) 5 gms was dissolved in water 50 ml at room temperature. Under stirring, at 50° C. 100 ml acetonitrile was added. Stirring was continued for 2 hour with gradual cooling. Stirring was further continued for 1 hour after the separation of the crystals. Filtration of the crystals and drying at 60° C. afforded the title compound with a yield of 4.0 gms (80%) and melting point 176-78° C.

Example 13

Donepezil oxalate (any form) 5 gms was dissolved in tetrahydrofuran 50 ml under heating at 50° C. Under stirring, at 40° C. 100 ml diisopropyl ether was added. Stirring was continued for 1 hour after the separation of the crystals at 15° C. Filtration of the crystals and drying at 60° C. afforded the title compound with a yield of 4.2 gms (86%) and melting point 177-78° C.

Example 14

Donepezil oxalate (any form) 5 gms was dissolved in dichloromethane 50 ml under heating at 50° C. Under stirring, at 40° C. 100 ml toluene was added. Stirring was continued for 1 hour after the separation of the crystals. Filtration of the crystals and drying at 60° C. afforded the title compound with a yield of 4.2 gms (86%) and melting point 177-78° C.

Example 15

Donepezil oxalate (any form) 5 gms was dissolved in dimethyl formamide 25 ml under heating at 50° C. Stirring was continued for 1 hour with gradual cooling. Stirring was further continued for 1 hour after the separation of the crystals at room temperature. Filtration of the crystals and drying at 60° C. afforded the title compound with a yield of 3.9 gms (78%) and melting point 176-78° C.

Example 16

Donepezil oxalate (any form) 5 gms was dissolved in dichloromethane 50 ml under heating at 50° C. Under stirring, at 40° C. 100 ml ethyl acetate was added. Stirring was continued for 1 hour with gradual cooling. Stirring was further continued for 1 hour after the separation of the crystals. Filtration of the crystals and drying at 60° C. afforded the title compound with a yield of 4.2 gms (86%) and melting point 176-78° C.

Example 17

Donepezil oxalate (any form) 5 gms was dissolved in water 60 ml under heating at 50° C. The reaction mass was kept for 72 hrs at RT. Filtration of the crystals and drying at 60° C. afforded the title compound with a yield of 4.1 gms (82%) and melting point 95.4-96° C. Water content 12.2% (By KF).

Example 18

Donepezil oxalate (any form) 5 gms was dissolved in mixture of water 50 ml and 10 ml methanol under heating at 50° C. The reaction mass was kept for 72 hrs at RT. Filtration of the crystals and drying at 60° C. afforded the title compound with a yield of 4.0 gms (80%) and melting point 95.5-96° C. Water content 12.4% (By KF).

SUMMARY

Given our teachings herein, one of skill in the art will without undue experimentation be able to make variations and modifications of the forgoing. Thus, while we discuss numerous specific examples here, we intend the scope of our patent to be defined not by any specific example(s) provided here, but by the appended claims.

Note that in the claims, we use the word "a" to mean at least one (i.e., perhaps more than one). Thus, for example, the claim phrase, "a compound selected from the group consisting of A, B and C" encompasses at least one of the enumerated compounds, and also encompasses combinations of more than one of these enumerated compounds (e.g., A and C together).

The invention claimed is:

1. Donepezil oxalate.

2. The composition of matter of claim 1, said composition of matter in a physical form having a physical characteristic selected from the group consisting of: a powder X-ray diffraction pattern as shown in FIG. 1; a powder X-ray diffraction pattern as shown. in FIG. 2; a .powder X-ray diffraction pattern as shown in FIG. 3; an infrared absorption spectrum as shown in FIG. 4, an infrared absorption spectrum as shown in FIG. 5; and an infrared absorption spectrum as shown in FIG. 6.

3. The composition of matter of claim 2, said physical form having a physical characteristic comprising: a powder X-ray diffraction pattern as shown in FIG. 1, and an infrared absorption spectrum as shown in FIG. 4.

4. The composition of matter of claim 2, said physical form having a physical characteristic comprising: a powder X-ray diffraction pattern as shown in FIG. 2, and an infrared absorption spectrum as shown in FIG. 5.

5. The composition of matter of claim 2, said physical form having a physical characteristic comprising: a powder X-ray diffraction pattern as shown in FIG. 3, and an infrared absorption spectrum as shown in FIG. 6.

6. Donepezil oxalate made by a process comprising:
   (a) dissolving donepezil base in a first solvent to make a first solution;
   (b) dissolving oxalic acid in a second solvent to make a second solution;
   (c) combining said first solution and said second solution to make a reaction mixture; and
   (d) isolating from said reaction a mixture a donepezil product.

7. The composition of matter of claim 6, said first solvent comprising ethyl acetate.

8. The composition of matter of claim 6, said second solvent selected from the group consisting of; acetone , propan-2-ol and methanol.

9. The composition of matter of claim 6, said isolating step comprising evaporating said first solvent and said second solvent.

10. The composition of matter of claim 6, said process further comprising:
    (e) dissolving said donepezil product in a third solvent to make a second reaction mixture; and
    (f) isolating from said second reaction mixture a donepezil polymorph.

11. The composition of matter of claim 10, said third solvent selected from the group consisting of: water, methanol and ethanol.

12. The composition of matter of claim 11, said third solvent comprising methanol and said isolating step comprising evaporating said third solvent from said second reaction mixture.

13. The composition of matter of claim 10, said isolating step comprising: mixing said second reaction mixture with an anti-solvent; whereby said donepezil polymorph precipitates from said second reaction.

14. The composition of matter of claim 13, said anti-solvent selected from the group consisting of: diethyl ether, di-isopropyl ether, acetone, propan-2-ol, n-hexane, and toluene.

15. The composition of matter of claim 10, said third solvent selected from the group consisting of: dimethyl formamide and dichloromethane.

16. The composition of matter of claim 15, said third solvent comprising dimethyl formamide and said isolating step comprising evaporating said third solvent from said second reaction mixture.

17. The composition of matter of claim 15, said isolating step comprising: mixing said second reaction mixture with an anti-solvent; whereby said donepezil polymorph precipitates from said second reaction.

18. The composition of matter of claim 17, said anti-solvent selected from the group consisting of: toluene and ethyl acetate.

19. The composition of matter of claim 11, said third solvent comprising aqueous methanol, said reaction mixture held at a temperature of about 40° C. to about 60° C., and said isolating step comprising evaporating said third solvent from said second reaction mixture.

20. The composition of matter of claim 11, said reaction mixture held at a temperature of about 25° C. and said isolating step comprising evaporating said third solvent from said second reaction mixture.

* * * * *